(12) United States Patent
Walker

(10) Patent No.: US 8,181,862 B1
(45) Date of Patent: May 22, 2012

(54) SYSTEM FOR PROVIDING IDENTIFICATION AND INFORMATION, METHOD OF USE THEREOF

(75) Inventor: Timothy T. Walker, Springdale, MD (US)

(73) Assignee: Solomon Systems, Inc., Springdale, MD (US)

( * ) Notice: Subject to any disclaimer, the term of this patent is extended or adjusted under 35 U.S.C. 154(b) by 0 days.

(21) Appl. No.: 13/270,672

(22) Filed: Oct. 11, 2011

(51) Int. Cl.
*G06K 5/00* (2006.01)

(52) U.S. Cl. .......................... 235/380; 235/375; 235/487

(58) Field of Classification Search .................. 235/380, 235/487, 375, 382.5, 382, 451, 492
See application file for complete search history.

(56) References Cited

U.S. PATENT DOCUMENTS

| | | | |
|---|---|---|---|
| 6,681,003 | B2 | 1/2004 | Linder et al. |
| 7,204,808 | B1 | 4/2007 | Friedman et al. |
| 7,434,724 | B2 | 10/2008 | Lane |
| 7,515,053 | B2 | 4/2009 | Klein |
| 7,761,261 | B2 | 7/2010 | Shmueli et al. |
| 2003/0016122 | A1 | 1/2003 | Petrick |
| 2003/0052788 | A1* | 3/2003 | Kwong-Tai Chung .... 340/573.1 |
| 2004/0140898 | A1* | 7/2004 | Reeves ....................... 340/573.1 |
| 2007/0074043 | A1* | 3/2007 | Lacey ........................... 713/186 |
| 2007/0158411 | A1* | 7/2007 | Krieg ............................ 235/380 |
| 2007/0229287 | A1* | 10/2007 | Morgan .................... 340/573.1 |
| 2008/0200774 | A1 | 8/2008 | Luo |
| 2010/0072280 | A1 | 3/2010 | McGill et al. |
| 2010/0298899 | A1 | 11/2010 | Donnelly et al. |
| 2011/0003610 | A1 | 1/2011 | Key et al. |

FOREIGN PATENT DOCUMENTS

JP 2003067488 3/2003

OTHER PUBLICATIONS

Ngail, E., et al., "Design of an RFID-based Healthcare Management System using an Information System Design Theory", Inf Syst Front, 2009, 11:405-417.

* cited by examiner

*Primary Examiner* — Edwyn Labaze
(74) *Attorney, Agent, or Firm* — Ping Wang; Andrews Kurth, LLP

(57) ABSTRACT

Embodiments of a system and method are disclosed for providing identification and medical information. The embodiments include collecting and storing medical biographical information of a subject, embedding the medical biographical information in a readable code of an object worn by or in the possession of the subject, and scanning the readable code of the object worn by or in the possession of the subject using a device to retrieve the medical biographical information of the subject. The medical biographical information allows medical professionals to obtain the subject's medical information in order to provide medical care.

17 Claims, 3 Drawing Sheets

SYSTEM FOR PROVIDING IDENTIFICATION AND INFORMATION, METHOD OF USE THEREOF

FIELD

This application generally relates to relates to a system and method for providing identification and/or information; in particular, medical information.

BACKGROUND

When a subject, to whom lacks the ability to effectively communicate needs urgent medical care, responders typically arrive at the scene within a short period of time without any information regarding the person in distress (i.e., subject). To properly provide medical care, the responders typically ask the subject relevant questions, such as current medications, allergies to medications, prior medical histories, i.e. surgeries, hospital visits, and other conditions. However, even if the subject is alert, he or she typically cannot provide accurate answers to such questions under the circumstances. Consequently, responders often provide urgent medical care without some medical history information. Likewise, after the subject is transported to a medical facility, doctors and other medical personnel at the hospital are not equipped with some of the medical history information regarding the subject, especially if the subject has never gone to the hospital before. Medical personnel may need to contact the subject's physician and/or other hospitals to get the needed information, which can cost time, and potentially life. Therefore, it is a great need for a system which can provide biographical information and allows medical professionals to obtain a subject's medical information.

SUMMARY

One aspect of the present application relates to a method for providing identification and medical information of a subject in a removable object, comprising: collecting and storing medical biographical information of the subject; embedding the medical biographical information in a readable code of the object that can be worn by or in the possession of the subject; and scanning the readable code of the object worn by or in the possession of the subject using a device to retrieve the medical biographical information of the subject, wherein the medical biographical information allows responders to obtain the subject's medical information in order to provide care and wherein the object is not linked to a medical sensor and is worn by the subject in a non-hospital setting.

Another aspect of the present application relates to a system for providing identification and medical information of a subject in a removable object, comprising: a database for collecting and storing medical biographical information of the subject; an object that can be worn by or in the possession of the subject, the object including a readable code that contains the medical biographical information; and a device for scanning the readable code of the object worn by or in the possession of the subject to retrieve the medical biographical information of the subject, wherein the medical biographical information allows responders to obtain the subject's medical information in order to provide care, wherein the object is not linked to a medical sensor and is worn by the subject in a non-hospital setting.

Another aspect of the present application relates to a non-transitory computer readable medium providing instructions for providing identification and medical information, the instructions comprising: collecting and storing medical biographical information of a subject; embedding the medical biographical information in a readable code of a removable object that can be worn by or in the possession of the subject; and scanning the readable code of the object worn by or in the possession of the subject using a device to retrieve the medical biographical information of the subject, wherein the medical biographical information allows responders to obtain the subject's medical information in order to provide medical care, wherein the object is not linked to a medical sensor and is worn by the subject in a non-hospital setting.

BRIEF DESCRIPTION OF THE DRAWINGS

The detailed description will refer to the following drawings, wherein like numerals refer to like elements.

DETAILED DESCRIPTION

Figure 1:
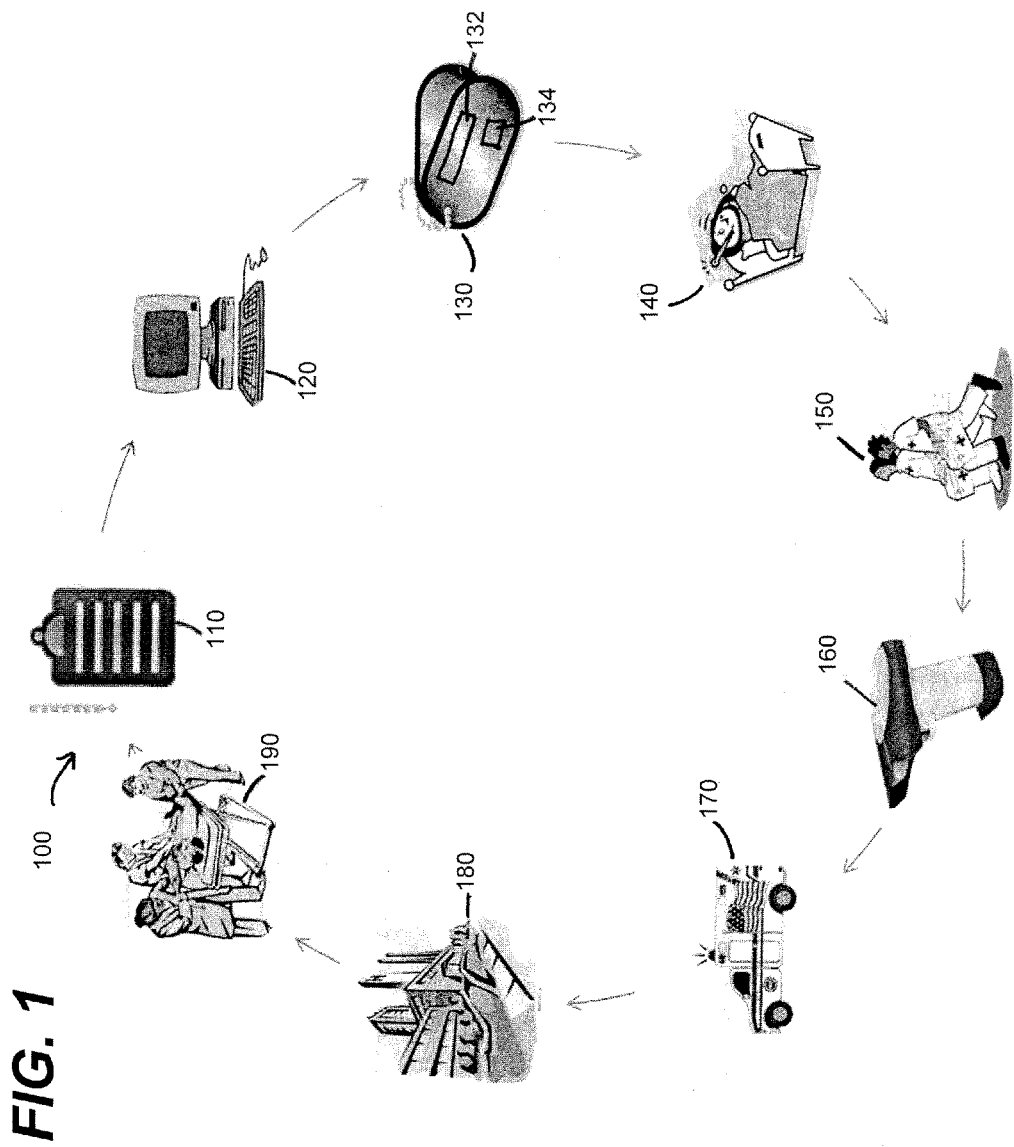
FIG. 1 illustrates an embodiment of the system for providing identification and medical information.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention.

Descriptions of specific applications are provided only as representative examples. The present application is not intended to be limited to the embodiments shown, but is to be accorded the widest possible scope consistent with the principles and features disclosed herein.

One aspect of the present application relates to a method for providing identification and medical information of a subject in a removable object, comprising: collecting and storing medical biographical information of the subject; embedding the medical biographical information in a readable code of the object that can be worn by or in the possession of the subject; and scanning the readable code of the object worn by or in the possession of the subject using a device to retrieve the medical biographical information of the subject, wherein the medical biographical information allows responders to obtain the subject's medical information in order to provide care and wherein the object is not linked to a medical sensor and is worn by the subject in a non-hospital setting.

In a particular embodiment, the method further comprises displaying the retrieved medical biographical information on a computer screen located in an emergency vehicle when the subject needs care.

In another particular embodiment, the method further comprises transmitting the retrieved medical biographical information to a medical facility that is designated to receive the subject.

In another particular embodiment, the method further comprises tracking the subject's location using a tracking circuit located on the object worn by or in the possession of the subject.

In another particular embodiment, the method further comprises updating the medical biographical information after the subject is treated at the medical facility.

The method of the present invention provides a convenient way for a subject to carry with the subject the subject's medical biographical information, such as current medications, allergies to medications, prior medical histories, and other conditions, in a non-hospital setting and preferably on a daily basis, so that such information can be retrieved in a medical facility (e.g., in a hospital or doctor's office) or during a medical emergency. The method allows the subject to quickly provide accurate medical biographical information on demand. Such information may be critical to a subject under urgent medical care. The information, however, is carried by the subject at will in a non-hospital setting and can be removed from the subject at any time. As used herein, the term "non-hospital setting" refers to settings, environments and surroundings that are not directly related to medical treatment or examination of a subject. Examples of "non-hospital setting" include, but are not limited to, work place, entertainment facilities and home. If the work place of the subject is a hospital, it is considered a "non-hospital setting" because the work place is not directly related to medical treatment or examination of the subject itself.

Another aspect of the present application relates to a system for providing identification and medical information of a subject in a removable object, comprising: a database for collecting and storing medical biographical information of the subject; an object that can be worn by or in the possession of the subject, the object including a readable code that contains the medical biographical information; and a device for scanning the readable code of the object worn by or in the possession of the subject to retrieve the medical biographical information of the subject, wherein the medical biographical information allows responders to obtain the subject's medical information in order to provide care, wherein the object is not linked to a medical sensor.

In a particular embodiment, the system further comprises a computer screen located in an emergency vehicle to display the retrieved medical biographical information.

In another particular embodiment, the system further comprises a transmitting the retrieved medical biographical information to a medical facility that is designated to receive the subject.

In another particular embodiment, the system further comprises a tracking circuit that is capable of tracking the subject's location.

In another particular embodiment, the medical biographical information is updated after the subject is treated at the medical facility.

In another particular embodiment, the medical biographical information include one or more of the subject's name, sex, date of birth, height, weight, blood type, allergies, sicknesses or medical conditions, use of medications, emergency contacts, and complete medical records.

In another particular embodiment, the object is a bracelet or a necklace worn by the subject.

In another particular embodiment, the database is located at a server.

In another particular embodiment, the medical biographical information is retrieved when the subject needs medical care.

In another particular embodiment, the medical biographical information is retrieved under emergency circumstances.

In another particular embodiment, the medical biographical information is retrieved under non-emergency circumstances.

Another aspect of the present application relates to a non-transitory computer readable medium providing instructions for providing identification and medical information, the instructions comprising: collecting and storing medical biographical information of a subject; embedding the medical biographical information in a readable code of a removable object that can be worn by or in the possession of the subject; and scanning the readable code of the object worn by or in the possession of the subject using a device to retrieve the medical biographical information of the subject, wherein the medical biographical information allows responders to obtain the subject's medical information in order to provide medical care, wherein the object is not linked to a medical sensor.

In a particular embodiment, the computer readable medium comprises instructions for displaying the retrieved medical biographical information on a computer screen located in an emergency vehicle when the subject needs medical care.

In another particular embodiment, the computer readable medium comprises instructions for transmitting the retrieved medical biographical information to a medical facility that is designated to receive the subject.

In another particular embodiment, the computer readable medium comprises instructions for tracking the subject's location using a tracking circuit located on the object worn by or in the possession of the subject.

As used herein, a "medical sensor" refers to a device or apparatus that measures or monitors a dynamic bodily function, process or condition. Examples of medical sensors are those that measure or monitor heart rate, temperature, blood oxygen or other blood gasses, an electrocardiogram, or an electroencephalogram.

As used herein, a "removable" object refers to an object that a subject or a person attending the subject can place on, or remove from, the body, clothing or an accessory (such as a wallet or in a purse or bag) of the subject at will. The removable object can be worn on a daily basis, at all times, or at only particular times chosen by the subject, such as, but not limited to, during sleep, exercise, at home, travel, work, outdoors, or indoors.

A system and method are disclosed to assist a medical professional or responder to identify and provide appropriate medication and care to subjects unable to communicate for themselves in non-emergency or emergency scenarios.

One aspect of the present application relates to a system for providing identification and information. In a particular embodiment, as illustrated in FIG. 1, the system 100 collects a subject's medical biographical information 110 from various sources, such as the subject's doctors' offices, medical facilities that the subject has visited in the past, and medical records or notes prepared or assembled by the subject. Examples of the subject's medical biographical information 110 include name, sex, date of birth, height, weight, blood type, allergies, sicknesses/medical conditions, use of prescribed medications, emergency contacts, as well as complete medical records if available.

In a particular embodiment, the system 100 electronically stores the subject's medical biographical information 110 in a database of a computer system 120. In some embodiments, the subject's medical biographical information 110 stored in the database is updated by the subject's doctors or the subject as needed. The system 100 embeds the stored subject's medical biographical information 110 in a readable code 132 of an object 130 that is worn by or in the possession of the subject 140. In some embodiments, the object 130 is a bracelet, pendant, dog tag, necklace, jewelry, button or other object that is worn by the subject.

In another embodiment, the object 130 is a card or a computer readable device, such as, but not limited to, a flash drive, solid state storage device, compact disc, or digital video disc (DVD). In particular embodiments, the object 130 is kept in the subject's wallet, purse or pocket.

In particular embodiments, a responder 150 uses a device 160 to scan the readable code 132 of the object 130 worn by, or in the possession of, the subject 140. In particular embodiments, the device 160 obtains the subject's medical biographical information 110, which may include, for example, the subject's name, sex, date of birth, height, weight, blood type, allergies, medical histories and conditions, sicknesses, use of prescribed medications, emergency contacts, as well as the complete medical records if available.

In particular embodiments, the responder 150 is a paramedic, emergency medical technician (EMT), fire fighter, policeman/woman, medical professional, or care worker. The term "medical professional" or "medical practitioner" as used herein, includes any person who cares for the medical needs of a subject such as, but not limited to, a physician, surgeon, dentist, chiropractor, osteopath, nurse, nurse's aide, orderly or volunteer.

In some embodiments, the device 160 is a handheld scanner. In other embodiments, the device 160 is a cellular telephone or a computer, including, but not limited to a laptop, pad or tablet computer. In particular embodiments, the device 160 includes an integrated display that displays the subject's medical biographical information 110 to assist the responder on the scene to provide care to the subject 140. in another embodiment, the obtained medical biographical information 110 is displayed on a computer or other device or equipment. In a particular embodiment, the device and/or display is located in an emergency vehicle 170.

In another embodiment, the system 100 transmits the medical biographical information 110 to a medical facility 180 that is designated to receive the subject 140. The designated medical facility 180 uses the medical biographical information 110 and the current medical needs of the subject 140 to develop a plan for medical care. In a particular embodiment, said plan for medical care is developed before the subject arrives at the designated medical facility 180.

In a particular embodiment, the medical facility 180 is a hospital. In another particular embodiment, the medical facility 180 is an emergency room. In another particular embodiment, the medical facility 180 is an outpatient facility, including an outpatient urgent care facility. In another particular embodiment, the medical facility 180 is a clinic. In another particular embodiment, the medical facility 180 is a nursing home. In another particular embodiment, the medical facility 180 is a physician's office. In yet another particular embodiment, the medical facility 180 is a dentist's office.

In particular embodiments, trans al of the medical biographical information 110 and the current medical needs of the subject 140 to the medical facility 180 allows a medical professional 190 at the medical facility 180 to be prepared for the subject's 140 arrival.

In particular embodiments, a medical professional 190 and/or responder 150 submits updated medical biographical information 110 to the database 120. In another embodiment, the subject submits updated medical biographical information 110 to the database 120. In particular embodiments, the updated medical biographical information 110 is automatically synced with data embedded in the readable code 132 of the object 130.

In a particular embodiment, the object 130 comprises a GPS or other tracking circuit 134. In particular embodiments, the medical professional 190 tracks the location of the subject 140. In a particular embodiment, the distance and the travel time before arrival at the medical facility 180 is determined.

In particular embodiments, the system 100 is used for emergency circumstances. In other particular embodiments, the system 100 is used for non-emergency circumstances. In a related embodiment, the non-emergency circumstance is transport of a subject 140 from one medical facility 180 to a different medical facility 180.

Figure 2:
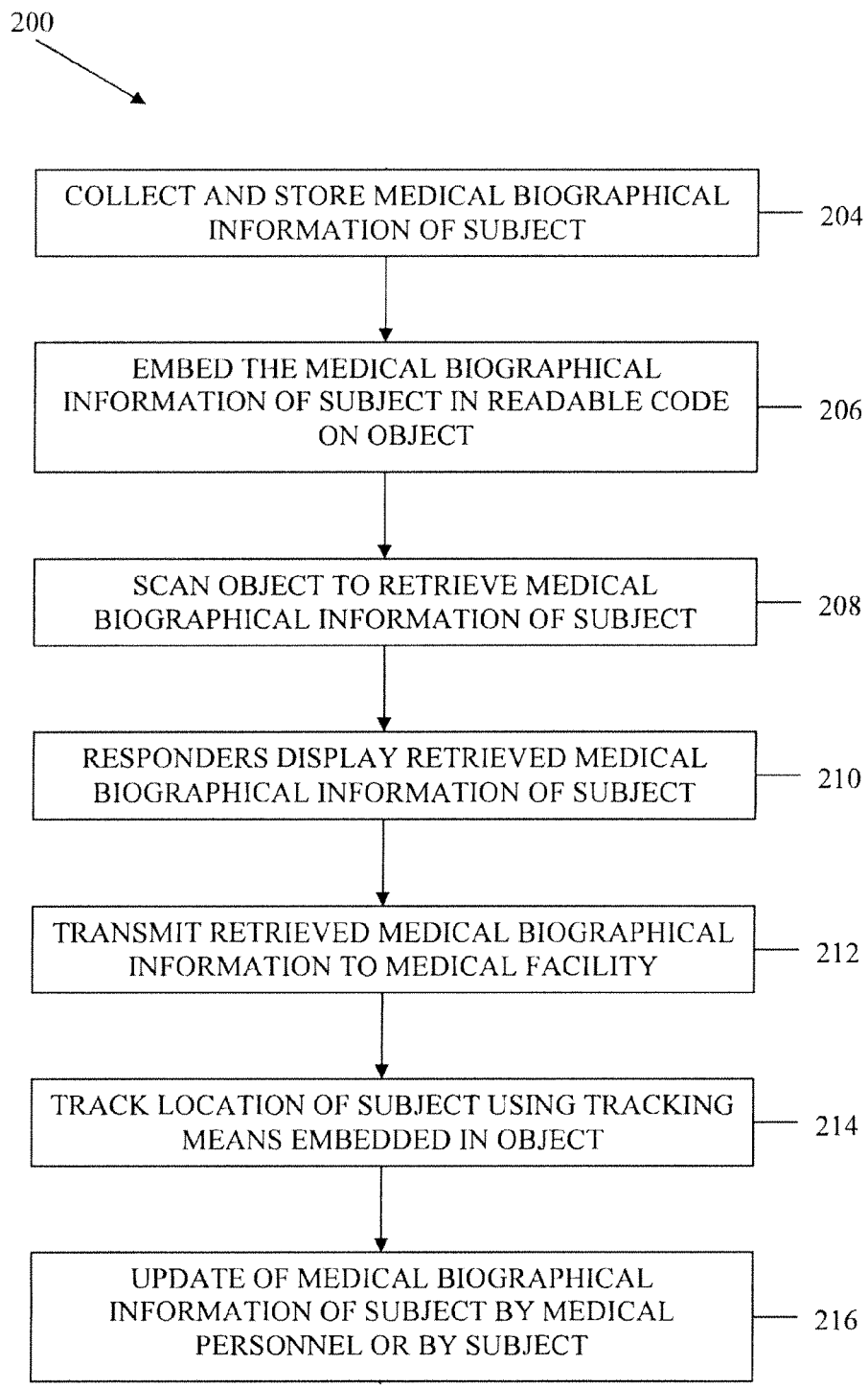
FIG. 2 is a flow charting illustrating an embodiment of the method for providing identification and medical information.

FIG. 2 is a flow chart showing a non-limiting example of an embodiment of a method 200 for providing identification and medical information. In a particular embodiment, method 200 comprises the collection and storage of medical biographical information of the subject 204. In a particular embodiment, the medical biographical information is embedded in a readable code of an object that can be worn by or in the possession of the subject 206. In particular embodiments, a device reads the readable code 208 of the object 206 to retrieve the medical biographical information of the subject 204. In some embodiments, the retrieved medical biographical information 204 is displayed on a computer screen located in an emergency vehicle 210. In particular embodiments, the retrieved medical biographical information 204 is wirelessly transmitted to a medical facility that is designated to receive the subject 212. In some embodiments, the location of the subject is determined using a GPS tracking circuit located on the object worn by the subject 214. In particular embodiments, the medical biographical information 204 is updated by a medical professional or responder 216.

Figure 3:
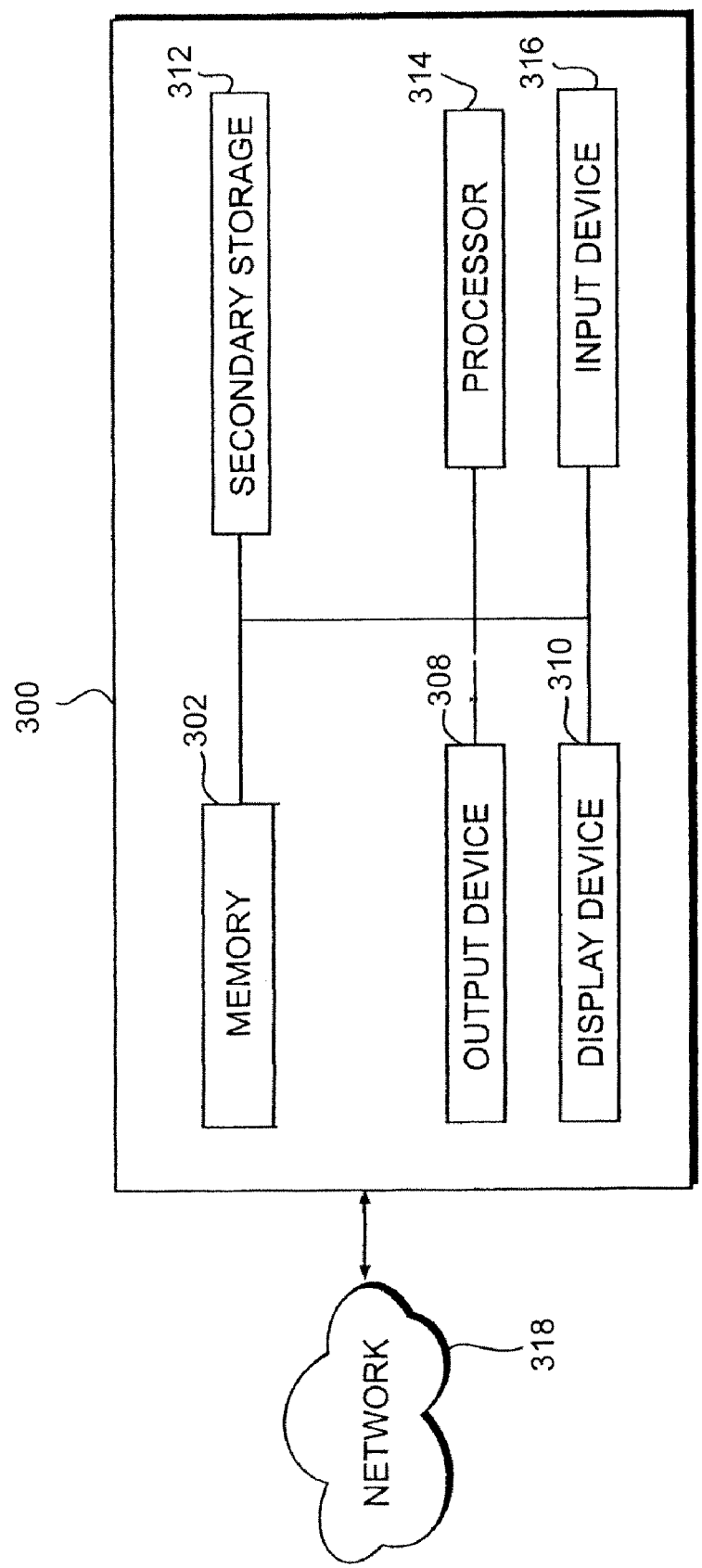
FIG. 3 is a block diagram illustrating exemplary hardware components of the exemplary computer system or server for implementing embodiments of the system and method for providing identification and medical information.

In particular embodiments, as illustrated in FIG. 3, the system disclosed in the present application comprises a computer system or server 300 for implementing embodiments of the system 100 (FIG. 1) and method 200 (FIG. 2) for providing identification and medical information. In an exemplary embodiment, the computer system or server 300 is the computer system 120 of FIG. 1. In particular embodiments, the computer system or server 300 includes and executes software programs to perform functions described herein, including the steps of the method 200 described above. In other embodiments, computer system 300 is a mobile device that performs the steps of the method 200 described above. In particular embodiments. The computer system 300 connects with a network 318 to receive inquires, obtain data, and transmit information as described above. In some embodiments, the network is the internet. In other embodiments, the network is an intranet, WAN, or LAN.

In an exemplary embodiment, the computer system 300 includes a memory 302, a processor 314, and, optionally, a secondary storage device 312. In some embodiments, the computer system 300 includes a plurality of processors 314 and is configured as a plurality of, e.g., bladed servers, or other known server configurations. In particular embodiments, the computer system 300 also includes an input device 316, a display device 310, and an output device 308. In some embodiments, the memory 302 includes RAM or similar types of memory. In particular embodiments, the memory 302 stores one or more applications for execution by the processor 314. In some embodiments, the secondary storage device 312 includes a hard disk drive, floppy disk drive, CD-ROM or DVD drive, or other types of non-volatile data storage. In particular embodiments, the processor 314 executes the application(s) that are stored in the memory 302 or the secondary storage 312, or received from the internet or other network 318. in some embodiments, processing by the processor 314 may be implemented in software, such as software modules, for execution by computers or other machines. These applications preferably include instructions executable to perform the functions and methods described above and illustrated in the Figures herein. The applications preferably provide GUIs through which users may view and interact with the application(s).

In some embodiments, the processor 314 may execute one or more software applications in order to provide the functions described in this specification, specifically to execute and perform the steps and functions in the methods described above. Such methods and the processing may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the system 100.

In particular embodiments, the input device 316 may include any device for entering information into the computer system 300, such as a touch-screen, keyboard, mouse, cursor-control device, microphone, digital camera, video recorder or camcorder. The input device 316 may be used to enter information into GUIs during performance of the methods described above. In some embodiments, the display device 310 may include any type of device for presenting visual information such as, for example, a computer monitor or flat-screen display, mobile device screen, or a printer. The display device 310 may display the GUIs and/or output from a software program. In particular embodiments, the output device 308 may include any type of device for presenting a hard copy of information, such as a printer, and other types of output devices include speakers or any device for providing information in audio form.

Exemplary embodiments of the computer system 300 include dedicated server computers, such as bladed servers, personal computers, laptop computers, notebook computers, palm top computers, network computers, mobile devices, or any processor-controlled device capable of executing a web browser or other type of application for interacting with the system.

In particular embodiments, the system 100 and/or method 200 may use multiple computer systems or servers as necessary or desired to support the users and may also use back-up or redundant servers to prevent network downtime in the event of a failure of a particular server. In addition, although aspects of an implementation consistent with the above are described as being stored in the memory 302, one skilled in the art will appreciate that these aspects can also be stored on or read from other types of computer program products or computer-readable media, such as secondary storage devices 312, including hard disks, floppy disks, or CD-ROM; DVD or other forms of RAM or ROM. In particular embodiments, the computer-readable media may include instructions for controlling a computer system, such as the computer system 300, to perform a particular method, such as the methods described above.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method for providing identification and medical information of a subject in a removable object, comprising:
    collecting and storing medical biographical information of the subject;
    embedding the medical biographical information in a readable code of the object that can be worn by or in the possession of the subject,
    scanning the readable code of the object worn by or in the possession of the subject using a device to retrieve the medical biographical information of the subject; and
    transmitting the retrieved medical biographical information and current medical needs of the subject to a medical facility that is designated to receive the subject, wherein said medical facility prepares for the subject's arrival and develops a plan for medical care;
    further wherein the medical biographical information allows responders to obtain the subject's medical information in order to provide care and wherein the object is not linked to a medical sensor and is worn by the subject in a non-hospital setting.

2. The method of claim 1, further comprising displaying the retrieved medical biographical information on a computer screen located in an emergency vehicle when the subject needs care.

3. The method of claim 1, further comprising tracking the subject's location using a tracking circuit located on the object worn by or in the possession of the subject.

4. The method of claim 1, further comprising updating the medical biographical information after the subject is treated at the medical facility.

5. A system for providing identification and medical information of a subject in a removable object, comprising:
    a database for collecting and storing medical biographical information of the subject; an object that can be worn by or in the possession of the subject, the object including a readable code that contains the medical biographical information; and
    a device for scanning the readable code of the object worn by or in the possession of the subject to retrieve the medical biographical information of the subject,
    wherein the medical biographical information allows responders to obtain the subject's medical information in order to provide care and transmit the retrieved medical biographical information and current medical needs of the subject to a medical facility that is designated to receive the subject, wherein said medical facility prepares for the subject's arrival and develops a plan for medical care;
    further wherein the object is not linked to a medical sensor and is worn by the subject in a non-hospital setting.

6. The system of claim 5, further comprising a computer screen located in an emergency vehicle to display the retrieved medical biographical information.

7. The system of claim 5, further comprising a tracking circuit that is for tracking the subject's location.

8. The system of claim 5, wherein the medical biographical information is updated after the subject is treated at the medical facility.

9. The system of claim 5, wherein the medical biographical information include one or more of the subject's name, sex, date of birth, height, weight, blood type, allergies, sicknesses or medical conditions, use of medications, emergency contacts, and complete medical records.

10. The system of claim 5, wherein the object is a bracelet or a necklace worn by the subject.

11. The system of claim 5, wherein the database is located at a server.

12. The system of claim 5, wherein the medical biographical information is retrieved when the subject needs medical care.

13. The system of claim 12, wherein the medical biographical information is retrieved under emergency circumstances.

14. The system of claim 12, wherein the medical biographical information is retrieved under non-emergency circumstances.

15. A non-transitory computer readable medium providing instructions for providing identification and medical information, the instructions comprising:
 collecting and storing medical biographical information of a subject;
 embedding the medical biographical information in a readable code of a removable object that can be worn by or in the possession of the subject;
 scanning the readable code of the object worn by or in the possession of the subject using a device to retrieve the medical biographical information of the subject,
 transmitting the retrieved medical biographical information and current medical needs of the subject to a medical facility that is designated to receive the subject, and preparation by the medical facility for the subject's arrival and develops a plan for medical care;
 wherein the medical biographical information allows responders to obtain the subject's medical information in order to provide medical care and wherein the object is not linked to a medical sensor and is worn by the subject in a non-hospital setting.

16. The computer readable medium of claim 15, comprising instructions for displaying the retrieved medical biographical information on a computer screen located in an emergency vehicle when the subject needs medical care.

17. The computer readable medium of claim 15, comprising instructions for tracking the subject's location using a tracking circuit located on the object worn by or in the possession of the subject.

* * * * *